United States Patent [19]

Tam

[11] Patent Number: 5,748,697
[45] Date of Patent: May 5, 1998

[54] METHOD AND APPARATUS FOR ELIMINATING BOUNDARY ERRORS IN CONE BEAM IMAGING

[75] Inventor: Kwok C. Tam, Edison, N.J.

[73] Assignee: Siemens Corporate Research, Inc., Princeton, N.J.

[21] Appl. No.: 771,401

[22] Filed: Dec. 20, 1996

[51] Int. Cl.⁶ .................................................. A61B 6/03
[52] U.S. Cl. .............................. 378/19; 378/15; 378/901
[58] Field of Search ........................ 378/4, 8, 15, 19, 378/901

[56] References Cited

U.S. PATENT DOCUMENTS 5,390,111  2/1995  Tam ........................................ 378/16
5,461,650  10/1995  Tam ........................................ 378/4

Primary Examiner—David P. Porta
Assistant Examiner—David Vernon Bruce
Attorney, Agent, or Firm—Lawrence C. Edelman

[57] ABSTRACT

In accordance with the principles of the present invention, image reconstruction errors which occur when using an area detector having a plurality of rows of detector elements defining a height for the detector that is smaller than the cone beam image, can be avoided by correlating an amount of orthogonal translation applied to line segments L extending across the detector towards top and bottom edges thereof that are used for calculating Radon derivative data, with the spacing between adjacent rows of the detector elements that are at the top and bottom edges of the detector. In a preferred embodiment the detector comprises a plurality of M rows of detector elements centered between the top and bottom edges of the detector, and an additional N rows of detector elements adjacent the M rows, at both of the top and bottom edges of the detector (where N may equal 1).

29 Claims, 4 Drawing Sheets

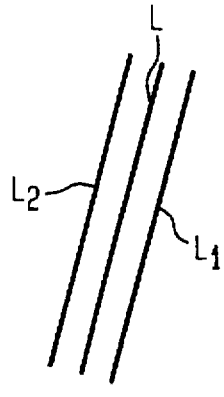
FIG. 3A
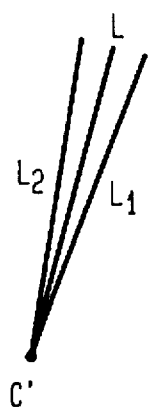
FIG. 3B
FIG. 6
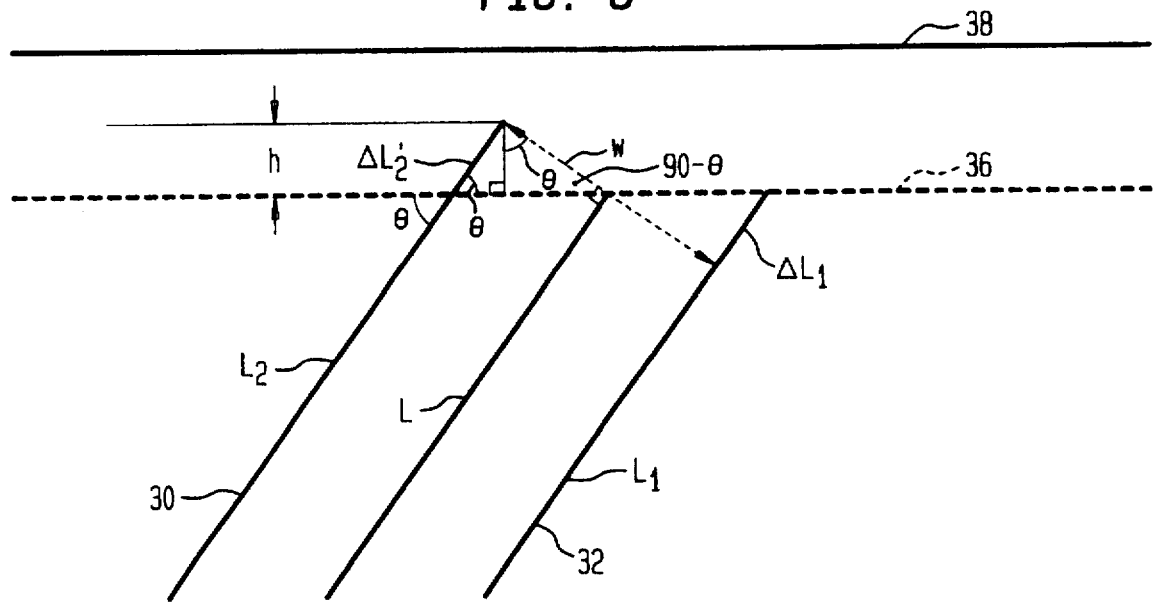

METHOD AND APPARATUS FOR ELIMINATING BOUNDARY ERRORS IN CONE BEAM IMAGING

BACKGROUND OF THE INVENTION

1. Field of the Invention

The present invention relates generally to three-dimensional (3D) computerized tomography (CT) and more specifically, to a method and apparatus for allowing the use of a relatively small area detector in a cone beam CT imaging apparatus without introducing detector boundary errors which would cause artifacts when reconstructing an image.

2. Description of the Background Art

In conventional computerized tomography for either of medical or industrial applications, an x-ray fan beam and a linear array detector are used to achieve two-dimensional (2D) imaging. While an acquired data set may be complete and image quality is correspondingly high, only a single slice of an object is imaged at a time. Thus, if a 3D image is required, an approach which acquires a stack of slices is employed. Acquiring a 3D data set one 2D slice at a time is inherently slow. Moreover, in medical applications, motion artifacts occur because adjacent slices are not imaged simultaneously. Also, dose utilization is less than optimal because the distance between slices is typically less than the x-ray collimator aperture, resulting in double exposure to many parts of the body. In 2D CT, the scanning path of the source is often simply a circular scan about the object.

More recently a system employing cone beam geometry has been developed for 3D imaging and includes a cone beam x-ray source instead of a fan beam source, and a 2D area detector instead of a linear array detector. An object to be imaged is scanned, preferably over a 360° angular range, either by moving the x-ray source in a scanning path about the object or by rotating the object while the source remains stationary. In either case, the area detector is fixed relative to the source and relative movement between the source and object provides the scanning (irradiation of the object by the cone beam energy). Compared to the conventional 2D "stack of slices" approach to achieve 3D imaging, the cone beam approach has the potential to achieve 3D imaging of both medical and industrial applications both rapidly and with improved dose utilization.

The 2D area detector used for 3D imaging generally has detector elements arranged in a 2D array of rows and columns. Available area detectors have generally been of large size and low quality, such as used with x-ray image intensifiers, or of small size and high quality. High cost and other factors have made large area 2D array detectors having high quality and high resolution, generally unavailable. In my earlier U.S. Pat. No. 5,390,112 entitled THREE-DIMENSIONAL COMPUTERIZED TOMOGRAPHY SCANNING METHOD AND SYSTEM FOR IMAGING LARGE OBJECTS WITH SMALL AREA DETECTORS issued Feb. 14, 1995, and hereby incorporated by reference, a cone beam CT system was disclosed in which an x-ray source following a spiral scan path is used to image a relatively long object, wherein the x-ray detector is much shorter than the object. The only height requirement for the detector is that it be longer than the distance between adjacent turns in the spiral scan of the x-ray source. A problem not taken into consideration in the forenoted patent is the fact that the cone beam image of the object extends beyond the boundaries of the detector, thereby causing errors when reconstructing an image of the object.

An object of the present invention is to reduce image reconstruction errors which occur when using an area detector that is smaller than the cone beam image.

SUMMARY OF THE INVENTION

In accordance with the principles of the present invention, image reconstruction errors which occur when using an area detector having a plurality of rows of detector elements defining a height for the detector that is smaller than the cone beam image, are avoided by correlating the amount of orthogonal translation applied to line segments L extending across the detector towards top and bottom edges thereof that are used for calculating Radon derivative data, with the spacing between adjacent rows of the detector elements that are at the top and bottom edges of the detector. In a preferred embodiment the detector comprises a plurality of M rows of detector elements centered between the top and bottom edges of the detector, and an additional N rows of detector elements adjacent the M rows, at both of the top and bottom edges of the detector (where N may equal 1).

BRIEF DESCRIPTION OF THE DRAWINGS

FIGS. 3a and 3b illustrate a portion of the procedure of FIG. 2;

FIG. 6 illustrates why, in one embodiment of the invention, only a single extra row of detector elements is needed at the top and bottom edges of the detector to eliminate errors in accordance with the present invention.

DETAILED DESCRIPTION OF THE PREFERRED EMBODIMENTS

Figure 1:
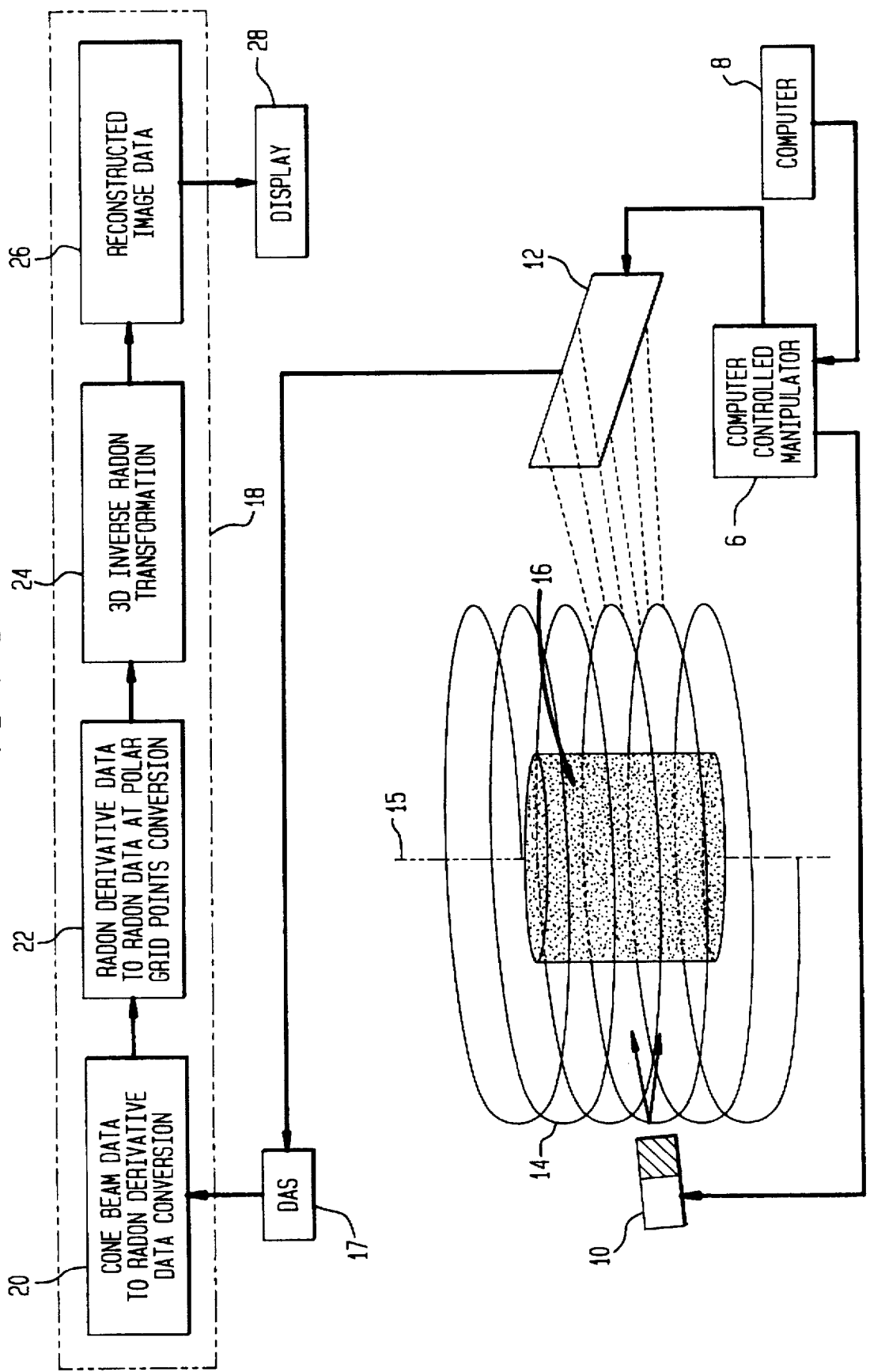
FIG. 1 is a simplified perspective illustration of the imaging of an object using an x-ray source and detector, combined with a simplified block diagram of image reconstruction according to the present invention.

FIG. 1 illustrates a cone beam 3D CT imaging system useful for carrying out the present invention, which is substantially the same, except as to be specifically described later, as known from my forenoted U.S. Pat. No. 5,390,112. As illustrated, a computer controlled manipulator 6, in response to control signals from an appropriately programmed computer 8, cause a source of cone beam energy 10 and a two-dimensional array detector 12 to cooperate along a defined source scanning trajectory, illustrated as a spiral scan path 14 centered on a predetermined axis 15 of an object 16, allowing detector 12 to acquire complete cone beam projection data for eventual reconstruction of an image of object 16. Computer 6, manipulator 8, source 10 and detector 12 cooperate in a manner generally well understood by those skilled in the art, i.e., such as described in detail in my forenoted U.S. Pat. No. 5,390,112, and therefore further details of their operation is not necessary. Alternatively, and equivalently, object 16 could be rotated to cause scanning by a fixed position source and detector. Furthermore, the scanning can be accomplished in a continuous or stepwise manner, and the spiral path can have equally spaced turns (sometimes referred to as stages), or turns with increasing pitch at the top and bottom edges of a region of interest of the object, such as described in my copending U.S. patent application Ser. No. 08/724,697 filed Sep. 30, 1996 entitled METHOD AND APPARATUS FOR SPIRAL SCAN REGION OF INTEREST IMAGING. Additionally, the object may be a work-piece, a medical patient, or other item for imaging. Furthermore, although source 10 is shown as an x-ray source, other types of imaging energy might be used, such as neutrons, positrons, etc.

Signals corresponding to the sensed x-ray energy falling on elements within detector 12 are supplied to a data acquisition system (DAS) 17 which, like the previously described portions of FIG. 1, may operate in a fashion well known to those of ordinary skill in this technology for digitizing, pre-processing, and storing of the cone beam projection data.

Cone beam projection data from the DAS 17 is supplied to a processor 18, which may be a computer programmed to perform various data conversions illustrated by the blocks within the processor 18. At block 20 the cone beam data is converted to Radon derivative data. This may be generally be accomplished using the techniques described in U.S. Pat. No. 5,257,183 entitled METHOD AND APPARATUS FOR CONVERTING CONE BEAM X-RAY PROJECTION DATA TO PLANAR INTEGRAL AND RECONSTRUCTING A THREE-DIMENSIONAL COMPUTERIZED TOMOGRAPHY (CT) IMAGE OF AN OBJECT issued Oct. 26, 1993, hereby incorporated by reference. However, as previously noted, and as will soon be described in greater detail, the conversion to derivative data as described in my forenoted U.S. Pat. No. 5,257,183 can introduce artifacts into the reconstructed image. At block 22 the Radon derivative data is converted to Radon data at polar grid points using, for example, the technique described in U.S. Pat. No. 5,446,776 entitled TOMOGRAPHY WITH GENERATION OF RADON DATA ON POLAR GRID POINTS issued Aug. 8, 1995, also hereby incorporated by reference. The Radon data at the polar grid points is supplied to block 24 which performs an inverse 3D Radon transformation using well known techniques, such as those described in detail in the fore-noted U.S. Pat. No. 5,257,183. At block 26 reconstructed image data is developed, and then fed from processor 18 to a display 28, which may operate in known fashion, to provide 3D CT imaging of object 16.

A more detailed description of the blocks of FIG. 1 can be found in the patents incorporated by reference herein.

Figure 2:
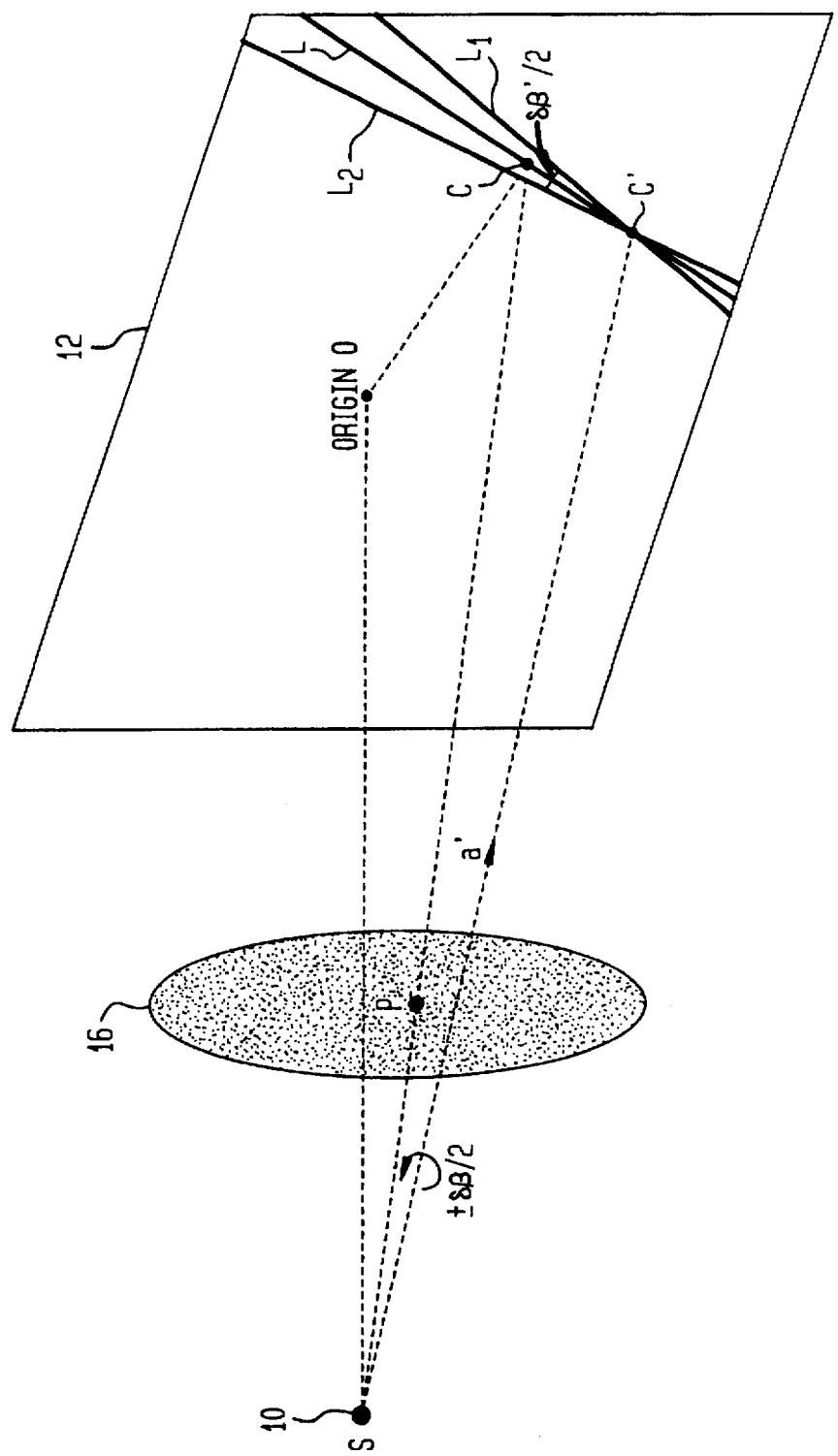
FIG. 2 illustrates a procedure for computing the radial derivative of the Radon data from the x-ray projection data.

Referring now to FIG. 2, a technique for developing the derivative of the radon data, such as described in detail in the forenoted U.S. Pat. No. 5,257,183, will next be briefly described. The improvement provided by the present invention finds particular use in this technique.

As previously noted, at block 20 the cone beam data is converted to Radon derivative data. As described in U.S. Pat. No. 5,257,183, one needs the object density planar integral value of the x-ray attenuation coefficient over a plane Q that intersects the source, object, and detector, in order to develop the radon data for each point in the object. FIG. 2 shows the result of a plane Q (not illustrated) intersecting the x-ray source 10, point P in the support (region in Radon space wherein the Radon transform of the object is non-zero), and detector 12. Plane Q intersects detector 12 at a line segment L. As described in detail in the forenoted U.S. Pat. No. 5,257,183, Radon data cannot be obtained by merely integrating the cone beam projection data along straight lines on a normalized detector plane. (However, if the data on the detector were generated by parallel beams of x-rays, integrating data along straight lines on the normalized detector plane would yield the Radon data.) The technique described in U.S. Pat. No. 5,257,183 for obtaining the Radon data from the integrated cone beam data is to rotate plane Q a small amount about any axis on the plane containing the origin O. The rotation allows introduction of a derivative value to the planar integral of the object density on plane Q by computation of the difference between weighted line integrals on a pair of adjacent line segments $L_1$ and $L_2$ on detector 12, where the line segments $L_1$ and $L_2$ are closely spaced to the line segment L and formed by rotated planes $Q_1$ and $Q_2$, respectively. This technique evaluates the radial derivative of the Radon data at a point P in the object, in accordance with the following steps:

1. Determine the plane Q passing through the point P and orthogonal to line OP.

2. Determine the line segment L where plane Q intersects the normalized detector plane.

3. Locate the point C on line segment L such that line SC is orthogonal to line segment L.

4. Take any point C' on line segment L, and define a rotation axis a' as a line from S to C'. Equivalently rotate plane Q about the rotation axis a' through a small angle $\pm\delta\beta/2$ resulting in planes $Q_1$ and $Q_2$, respectively, and rotate line segment L about point C' through a small angle $\pm\delta\beta/2$ on the detector plane, resulting in line segments $L_1$ and $L_2$, respectively. The planes $Q_1$ and $Q_2$ intersect the normalized detector plane 12 at the line segments $L_1$ and $L_2$, respectively.

5. Compute the quantities $J_1$ and $J_2$ on line segments $L_1$ and $L_2$.

6. Compute the angle $\delta\beta$ from the angle $\delta\beta'$ by geometry.

7. Then, the radial derivative of the Radon data at point P is obtained from the quantities $J_1$, $J_2$, and $\delta\beta$ using the following equation:

$$R'(P) = \frac{J_2 - J_1}{\delta\beta}$$

Using the above procedure, the Radon data can be obtained for all planes passing through the object irradiated by the cone beam source. However, this procedure only yields a good approximation of the derivative of the object density planar integral if the following conditions are satisfied:

1. The spacing between line segments $L_1$ and $L_2$ is small; and

2. Line segments $L_1$ and $L_2$ are of equal length and each is generated from line segment L by either a translation orthogonal to line segment L or a rotation operation about point C', as illustrated in FIGS. 3a and 3b, respectively. The equivalency of these operations can be easily understood by imagining point C' being infinitely far from point C.

In most prior art cone beam systems, condition (2) is not crucial because each of the line segments L, $L_1$ and $L_2$ usually extend beyond the cone beam image, and thus the detector values on the end portions of line segments $L_1$ and $L_2$ are zero. Thus, their contributions to the weighted integrals are zero and of no effect.

Figure 4:
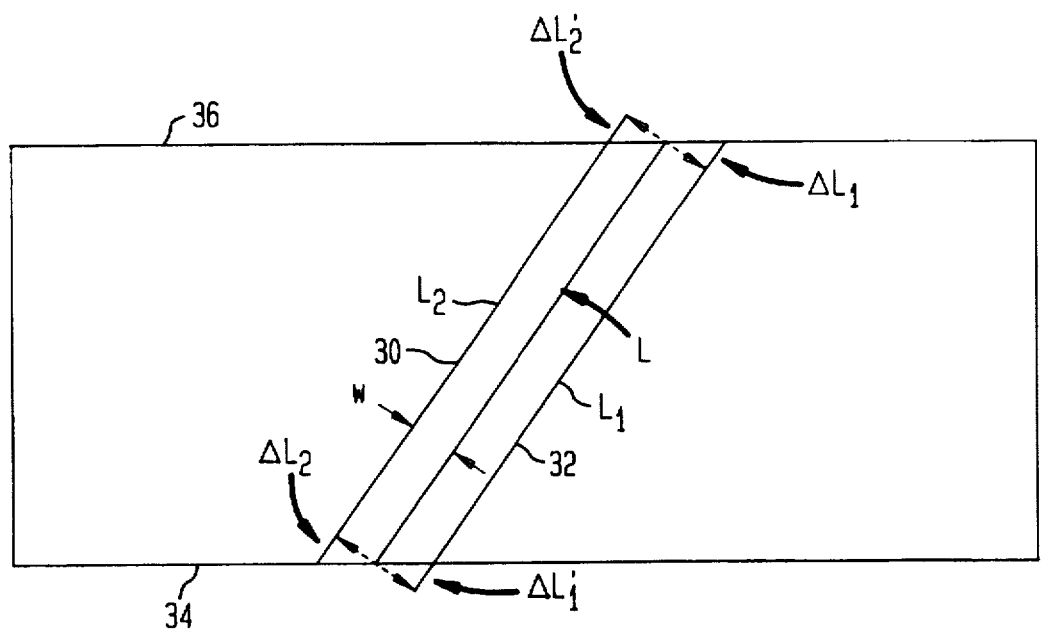
FIG. 4 illustrates the intersection of an integration plane with an x-ray detector to form line segments on the detector used for computing the derivative of the Radon data from the x-ray projection data in accordance with the procedure of FIG. 2.

However, in a cone beam spiral scan system such as shown in FIG. 1, the object is bigger than the field of view established by detector 12, and therefore the cone beam image extends past the top and bottom edges of detector 12. This situation is illustrated in greater detail in FIG. 4 wherein closely spaced lines 30, L and 32 are shown. Line segments $L_1$ and $L_2$ are of equal length and each is generated from line L located therebetween by translation of an amount w in opposite directions orthogonal to line segment L (as generally shown in FIG. 3a). However, as evident from FIG. 4, orthogonal translation from line segment L (indicated by dashed lines) results in an end portion of each of line segments $L_1$ and $L_2$, i.e., $\Delta L_1'$ and $\Delta L_2'$, that extends past the bottom 34 and top 36 edges, respectively, of detector 12. Furthermore, an end portion $\Delta L_1$ of line 32 has no corresponding portion on line 30 (i.e., no portion having a similar spatial position), and an end portion $\Delta L_2$ of line 30 has no corresponding portion on line 32, thus they cannot be used as replacements for the lost line segments $\Delta L_1'$ and $\Delta L_2'$. Additionally, since the cone beam image extends beyond the top 36 and bottom 34 edges of detector 12, the intensity values acquired by the elements of detector 12 in line portions $\Delta L_1$ and $\Delta L_2$ are non-zero.

Consequently, use of these non-zero intensity values from line portions $\Delta L_1$ and $\Delta L_2$ will cause errors when computing the derivative of the planar integral on the Q planes which intersect the detector at lines 30 and 32. For simplicity, such errors shall be referred to as boundary errors. For detectors having a reduced height, such as the spacing between adjacent turns of a spiral scan path, the length of line portions $\Delta L_1$ and $\Delta L_2$ becomes significant with respect to the length of line segments $L_1$ and $L_2$, and therefore the boundary errors become significant. Note, for line segments $L_1$ and $L_2$ generated by a rotation operation of the type shown in FIG. 3b, such boundary errors are not significant, since, as described in my U.S. Pat. No. 5,341,460, entitled METHOD AND APPARATUS FOR PRODUCING A THREE-DIMENSIONAL COMPUTERIZED TOMOGRAPHY IMAGE OF AN OBJECT WITH IMPROVED CONVERSION OF CONE BEAM DATA TO RADON DATA, issued Aug. 23, 1994, incorporated herein by reference, the term (t-$\Delta$C) is in the denominator of the equation defining the line integral J. The term (t-$\Delta$C) is representative of the distance between C' and P, and therefore the larger the distance between C' and P, the smaller and line integral value for that point. Consequently, the contribution to the line integral values by the $\Delta L_1$ and $\Delta L_2$ portions at the ends of line segments $L_1$ and $L_2$ becomes insignificant because points on these portions are the farthest from the point C', where lines $L_1$ and $L_2$ intersect.

Figure 5:
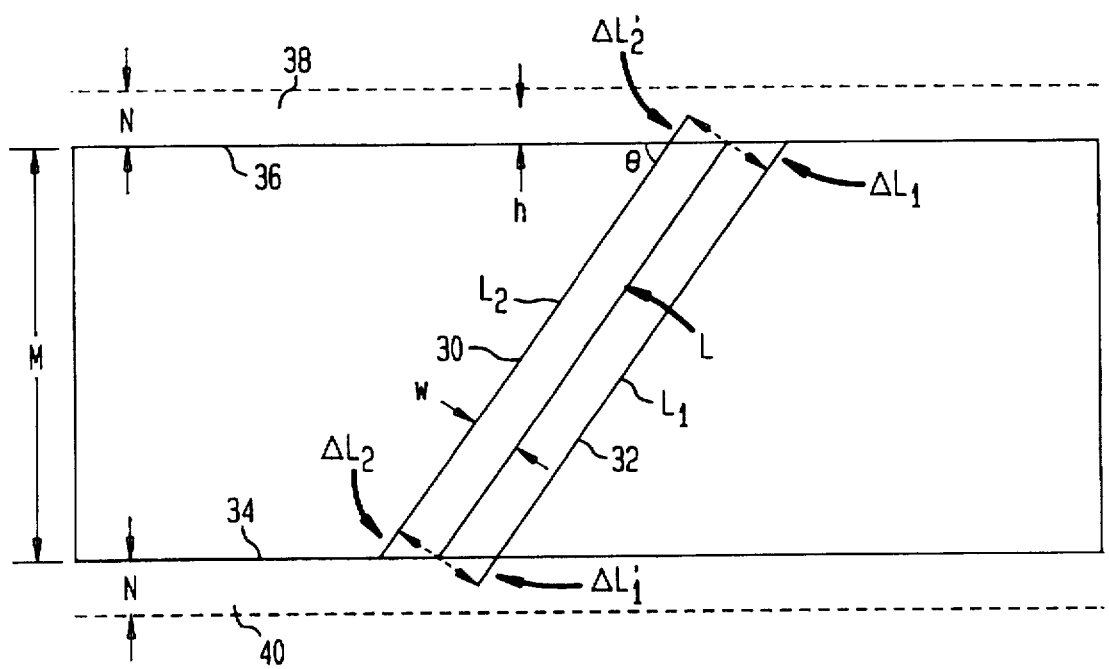
FIG. 5 illustrates manipulation of the line segments on the detector in accordance with the principles of the present invention for computing the derivative of the Radon data from the x-ray projection data.

In accordance with the principles of the present invention, the errors caused by loss of line portions $\Delta L_1'$ and $\Delta L_2'$ can be avoided in a cost effective manner by adding N (where N may equal 1) detector rows above the top edge 36 of detector 12, and another N (where N may equal 1) detector rows below the bottom edge 34 of detector 12, and correlating the amount of orthogonal translation from line segment L used for generating line segments $L_1$ and $L_2$, to be less than or equal to N times the spacing between said N rows of the detector elements that are adjacent said M rows. In a most cost effective preferred embodiment, the spacing between all of the rows of detector elements that comprise detector 12 is uniform, only a single extra row of detector elements is added at the top and bottom edges of detector 12, and the spacing between line segment L and either of line segments $L_1$ and $L_2$ is controlled so as to be less than or equal to one times the spacing between adjacent rows of the detector elements. This is illustrated in FIG. 5, wherein an extra N rows of detector elements (wherein N may equal 1) is added to the M rows of detector elements between the former top edge 36 and former bottom edge 34 of detector 12. In one embodiment, M may be equal to, for example 80, and each row may be, for example, 500 to 1000 elements long. Note that the M rows of the useful detector region are determined by the spiral pitch, as illustrated in FIG. 5. Thus, in accordance with the prior art technique, only the cone beam data bound by these M rows would be needed to compute the object density planar integral. The data on the two added detector rows would be redundant, if it were not for their use in accordance with the principles of the present invention, to eliminate the boundary errors.

Referring again to FIG. 5, in accordance with the principles of the present invention, when computing the weighted line integrals, projection data from portion $\Delta L_1$ of line 32 is not used, and projection data from portion $\Delta L_2'$ of line 30 is used, so that the upper ends of line segments $L_1$ and $L_2$ are orthogonally even with the upper end of line segment L. Similarly, projection data from portion $\Delta L_2$ of line 30 is not used, and projection data from portion $\Delta L_1'$ of line 32 is used, so that the lower ends of line segments $L_1$ and $L_2$ are orthogonally even with the lower end of line segment L. After these operations, the two line segments $L_1$ and $L_2$ satisfy condition (2) specified above (i.e., both are of equal length, and both orthogonally translated from L), and therefore the boundary errors that would have resulted during conversion of the projection data to Radon data using a detector having only M rows, is avoided.

Furthermore, with proper selection of the translation distance between line segments $L_1$, L and $L_2$, in a cost effective preferred embodiment, only one detector row is needed to be added to the top and bottom edges, respectively, of detector 12. As shown in FIG. 6 (which is an enlargement of that portion of FIG. 5 about the segment $\Delta L_2'$), let w be the spacing between line segments $L_1$ and L and between $L_2$ and L, and let h be the height $\Delta L_2'$ and $\Delta L_1'$ protrude above the top edge and below the bottom edge, respectively, of detector 12. It is easy to see that $$h = w \cos \theta$$

where $\theta$ is the angle line segments $L_1$, L and $L_2$ make with the rows of detector elements in detector 12. Since the maximum variation of $\cos\theta$ is 1, we have $h \leq w$. Consequently, when w is chosen to be smaller than the spacing between the lines of the detector elements, we have $h \leq 1$ detector row spacing. This result shows that the two added end portions $\Delta L_1'$ and $\Delta L_2'$ are contained within the area bounded by a single additional detector row 38 and 40, respectively, adjacent the former top and bottom edges 36 and 34, respectively, of detector 12.

Thus, there has been shown and described a novel method and apparatus for allowing the use of a relatively small area detector in a cone beam CT imaging apparatus without introducing detector boundary errors which would cause artifacts when reconstructing an image. Many changes, modifications, variations and other uses and applications of the subject invention will, however, become apparent to those skilled in the art after considering this specification and its accompanying drawings, which disclose preferred embodiments thereof. For example, the M detector rows could span more than 2 stages of the spiral path, such as 3 stages, but spanning of 2 stages would be the most cost effective embodiment. Furthermore, although in the illustrated embodiment the M detector rows have been evenly spaced, in some applications unevenly spaced rows of detector elements may be desirable. Additionally, the spacing between the M rows may be uniform, but a different spacing may be used for the N rows of elements adjacent the M rows that is more or less than the spacing between the M rows. All such changes, modifications, variations and other uses and applications which do not depart from the spirit and scope of the invention are deemed to be covered by this patent, which is limited only by the claims which follow as interpreted in light of the foregoing description.

I claim:

1. A scanning and data acquisition method for three dimensional (3D) computerized tomography (CT) imaging of an object in a field of view radially centered on a predetermined axis, the method comprising the steps of:

applying cone beam energy from a cone beam source to at least a portion of the object;

defining a source scanning trajectory as a path traversed by the source;

using the cone beam source, fixed relative to an area detector with both source and detector movably positioned relative to the object, to scan about the object;

specifying the source scanning trajectory as a spiral path defining a plurality of spaced stages on a predetermined geometric surface surrounding the field of view such that each plane passing through the field of view intersects the scanning trajectory in at least one point and intersects the area detector along a line segment L that extends towards top and bottom edges of the area detector, the area detector comprising a plurality of detector elements arranged in an array of rows and columns and having a predetermined number M of rows of detector elements between the top and bottom edges that extend sufficiently along a direction generally parallel to the predetermined axis so as to span at least two consecutive stages of the spiral path having the largest spacing therebetween, plus an extra N rows of detector elements adjacent both of the top and bottom edges of the detector, where N is greater than or equal to 1;

scanning at a plurality of positions along the source scanning trajectory to cause the detector elements of said area detector to acquire cone beam projection data corresponding to respective portions of the object;

calculating Radon derivative data by processing line integral values from cone beam projection data in adjacent detector line segments $L_1$ and $L_2$ that are parallel to line segment L and translated in an orthogonal direction therefrom by an amount which is less than or equal to N times the spacing between said extra N rows of detector elements contained in said area detector, where N is greater than of equal to 1; and reconstructing an image of the object using said Radon derivative data.

2. The method of claim 1, wherein N=1.

3. The method of claim 1, wherein said reconstructing step includes performing an inverse Radon transformation of said Radon derivative data.

4. The method of claim 1, wherein said calculating step is repeated so as to develop Radon derivative data for all points in the Radon space of said object in the field of view.

5. The method of claim 1, wherein said calculating step is repeated for a plurality of closely spaced line segments L developed as a result of the intersection of said detector with a respective plurality of rotated planes that pass through the field of view and also intersect the scanning trajectory in at least one point.

6. The method of claim 1, wherein said calculating step is repeated at each of said plurality of positions along the source scanning trajectory provided by said scanning step.

7. The method of claim 4, wherein said calculating step is repeated at each of said plurality of positions along the source scanning trajectory provided by said scanning step.

8. The method of claim 5, wherein said calculating step is repeated at each of said plurality of positions along the source scanning trajectory provided by said scanning step.

9. The method of claim 1, wherein said source provides x-ray energy.

10. A method in accordance with claim 1, wherein the geometric surface surrounding the field of view is cylindrical.

11. A method in accordance with claim 1, wherein said using step comprises moving the source along the scanning trajectory in a step-wise scan.

12. A method in accordance with claim 1, wherein said using step comprises moving the source along the scanning trajectory in a continuous scan.

13. A method in accordance with claim 1, wherein the step of using the cone beam source comprises maintaining the source and detector in stationary positions while translating and rotating the object so as to effect relative movement of the source with respect to the object.

14. A method in accordance with claim 1, wherein the step of using the cone beam source comprises maintaining the object in a stationary position while moving the source and detector to achieve relative movement of the source with respect to the object.

15. A method in accordance with claim 1, wherein the step of using the cone beam source comprises translating the object while rotating the source and detector to achieve spiral relative movement of the source with respect to the object.

16. A scanning and data acquisition system for three dimensional (3D) computerized tomography (CT) imaging of an object in a field of view radially centered on a predetermined axis, comprising:

a cone beam source for applying cone beam energy to at least a portion of the object;

a two-dimensional area detector positioned to receive cone beam energy from the source, the area detector comprising a plurality of detector elements arranged in an array of rows and columns and having a predetermined number M of rows of detector elements between top and bottom edges thereof that extend along a direction generally parallel to the predetermined axis, plus an extra number N rows of detector elements adjacent both of the top and bottom edges thereof, where N is greater than or equal to 1;

a scanning device operatively coupled to one of the object or the source and area detector for causing relative motion between the source and the object such that the source moves along a scanning trajectory relative to the object;

trajectory defining apparatus operatively coupled to the scanning device to cause the scanning device to provide as said scanning trajectory a spiral path defining a plurality of spaced stages on a predetermined geometric surface surrounding the field of view such that each plane of a plurality of planes passing through the field of view intersects the scanning trajectory in at least one point and intersects the area detector along a line segment L that extends towards top and bottom edges of the area detector, said predetermined number M of rows of detector elements of the area detector spanning at least two consecutive stages of the spiral path having the largest spacing therebetween;

beam energy detecting apparatus for acquiring cone beam projection data in response to said source being at a plurality of positions along the source scanning trajectory, said cone beam projection data corresponding to respective portions of the object;

a processor for calculating Radon derivative data from cone beam projection data in adjacent detector line segments $L_1$ and $L_2$ that are parallel to line segment L and translated in an orthogonal direction therefrom by an amount which is less than or equal to N times the spacing between said extra N rows of detector elements contained at the top and bottom edges, respectively, of said area detector, where N is greater than or equal to 1; and means for reconstructing an image of the object using said Radon derivative data.

17. The system in accordance with claim 16, wherein said M rows of detector elements span at least two stages, but less than four stages defined by said spiral path.

18. The system in accordance with claim 16, wherein N=1.

19. The system in accordance with claim 16, wherein said means for reconstructing an image includes a display for displaying an image of the object based upon said Radon Derivitive data.

20. The system in accordance with claim 16, wherein said means for reconstructing an image includes a processor for performing an inverse Radon transformation of said Radon derivative data.

21. The system in accordance with claim 16, wherein said processor repeats said calculation of Radon derivative data for a plurality of closely spaced line segments L developed as a result of the intersection of said detector with a respective plurality of rotated planes that pass through the field of view and also intersect the scanning trajectory in at least one point.

22. The system in accordance with claim 16, wherein said processor repeats said calculation of Radon derivative data as to develop Radon derivative data for all points in the Radon space of said object in the field of view.

23. The system in accordance with claim 21, wherein said processor repeats said calculation of Radon derivative data as to develop Radon derivative data for all points in the Radon space of said object in the field of view.

24. The system in accordance with claim 16, wherein said cone beam source comprises a source of x-ray energy.

25. The system in accordance with claim 16, wherein said scanning device causes the source to move along the scanning trajectory in a continuous scan.

26. The system in accordance with claim 16, wherein said scanning device causes the source to move along the scanning trajectory in a step-wise scan.

27. The system in accordance with claim 16, wherein said scanning device maintains the source and detector in stationary positions while translating and rotating the object so as to effect relative movement of the source with respect to the object.

28. The system in accordance with claim 16, wherein said scanning device maintains the object in a stationary position while moving the source and detector to achieve relative movement of the source with respect to the object.

29. The system in accordance with claim 16, wherein said scanning device translates the object while rotating the source and detector to achieve spiral relative movement of the source with respect to the object.

* * * * *